(12) United States Patent
Cinquemani

(10) Patent No.: US 10,206,829 B2
(45) Date of Patent: Feb. 19, 2019

(54) FLEECE FOR SUSTAINED RELEASE OF AN ACTIVE SUBSTANCE

(71) Applicant: Claudio Cinquemani, Cologne (DE)

(72) Inventor: Claudio Cinquemani, Cologne (DE)

(73) Assignee: REIFENHAEUSER GMBH & CO, KG MASCHINENFABRIK, Troisdorf (DE)

( * ) Notice: Subject to any disclaimer, the term of this patent is extended or adjusted under 35 U.S.C. 154(b) by 834 days.

(21) Appl. No.: 14/558,397

(22) Filed: Dec. 2, 2014

(65) Prior Publication Data

US 2015/0157514 A1 Jun. 11, 2015

(30) Foreign Application Priority Data

Dec. 10, 2013 (EP) .................... 13196502

(51) Int. Cl.
| | |
|---|---|
| *A61F 13/53* | (2006.01) |
| *A61F 13/15* | (2006.01) |
| *A61L 15/42* | (2006.01) |
| *A61L 15/22* | (2006.01) |
| *D04H 3/007* | (2012.01) |
| *D01D 5/08* | (2006.01) |
| *D01D 5/088* | (2006.01) |
| *D01D 5/247* | (2006.01) |
| *D01D 5/34* | (2006.01) |
| *D01F 1/08* | (2006.01) |

(52) U.S. Cl.
CPC ........ *A61F 13/53* (2013.01); *A61F 13/15617* (2013.01); *A61L 15/22* (2013.01); *A61L 15/425* (2013.01); *D01D 5/082* (2013.01); *D01D 5/088* (2013.01); *D01D 5/247* (2013.01); *D01D 5/34* (2013.01); *D01F 1/08* (2013.01); *D04H 3/007* (2013.01); *A61F 2013/530635* (2013.01); *Y10T 428/2395* (2015.04)

(58) Field of Classification Search
CPC ........................................................ D01D 5/34
USPC .............. 264/171.1, 172.11, 172.15, 172.17
See application file for complete search history.

(56) References Cited

U.S. PATENT DOCUMENTS

| | | | | |
|---|---|---|---|---|
| 4,434,204 A | * | 2/1984 | Hartman ................ | D04H 3/005 428/198 |
| 4,485,141 A | * | 11/1984 | Fujimura ............... | D01D 5/247 264/45.9 |
| 5,112,940 A | * | 5/1992 | Korte .................... | C08G 63/60 528/301 |
| 5,356,405 A | * | 10/1994 | Thompson ........ | A61F 13/15203 604/358 |

FOREIGN PATENT DOCUMENTS

EP 2093313 A1 8/2009

\* cited by examiner

*Primary Examiner* — Monica A Huson
*Assistant Examiner* — Kelsey C Grace
(74) *Attorney, Agent, or Firm* — Andrew Wilford

(57) ABSTRACT

The invention relates to the use of a fleece composed of plastic filaments, in particular made of a thermoplastic, as a sustained-released system or as a storage system for at least one active substance, in particular for at least one active liquid. The filaments are spun using a spinneret, and the plastic material of the filaments is foamed so that pores are formed at least on the surface or in surface regions of the filaments and at least some of the pores are pores that are open outward, and at least some of the open pores are filled with the active substance, in particular with the active liquid.

17 Claims, 3 Drawing Sheets

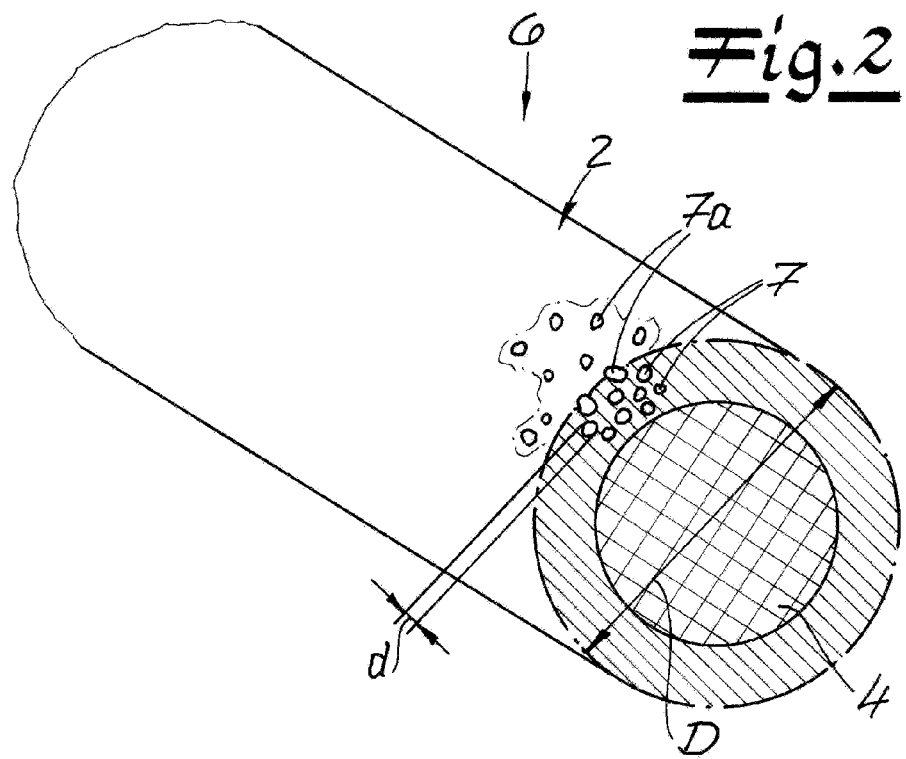
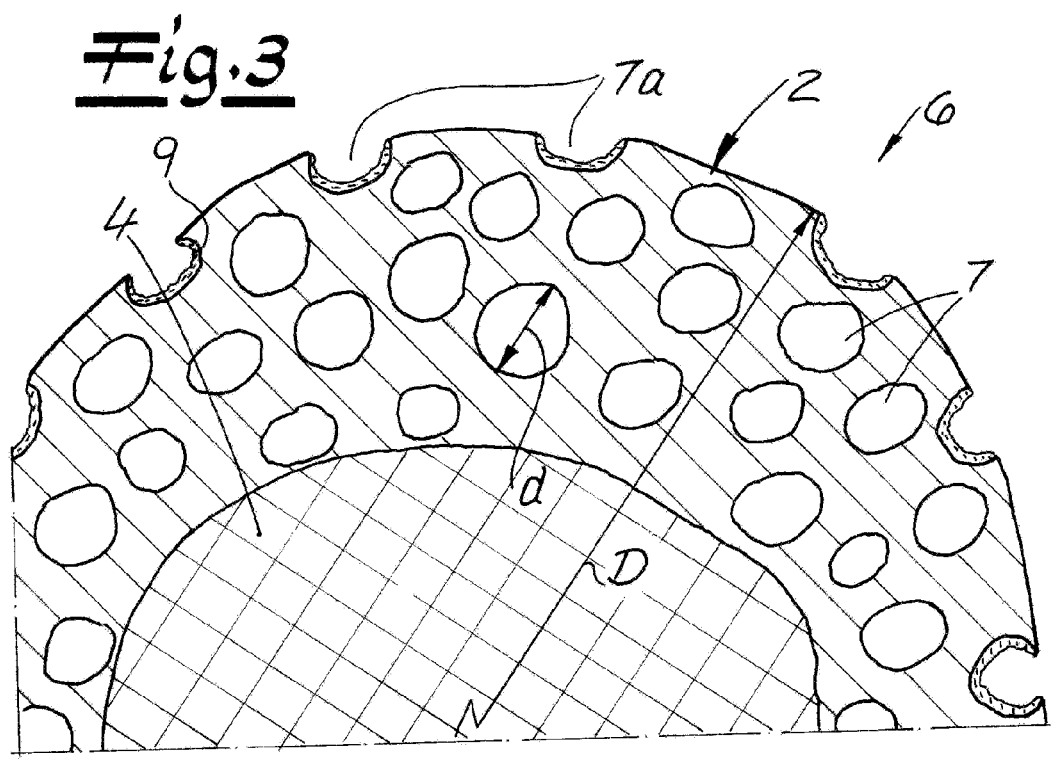

FLEECE FOR SUSTAINED RELEASE OF AN ACTIVE SUBSTANCE

The invention relates to the use of a fleece composed of plastic filaments, in particular made of a thermoplastic, as a sustained-released system or as a storage system for at least one active substance, in particular for at least one active liquid. The invention further relates to a corresponding fleece composed of plastic filaments, in particular made of a thermoplastic.

Uses of the above-described type are known from practical applications in various embodiments. In principle, it is also known and desirable to modify the properties of fleeces, and more particularly with the aid of special active substances. For example, it is desirable to hydrophilically modify the fleeces for use of them in a hygiene or sanitary product. It can also be desirable to hydrophobically modify the fleeces. In principle, it is known to apply active substance-containing liquid media to a fleece composed of fibers made of polypropylene or similar plastic materials.

A fleece made of polypropylene fibers initially has hydrophobic properties. It is known to apply what are known as permanent conditioning agents to such a fleece so as to adjust hydrophilic properties of this fleece. The term "permanent" indicates that the conditioning agent or the active substance is not readily or quickly rinsed by the aqueous media or the like applied to the fleece. Successful hydrophilic modification of such a fleece ensures a relatively short strike-through time of an aqueous media into this fleece is ensured. Such a short strike-through time is desirable in layers of fleece for diapers, for example. It is advantageous here if the strike-through time of urine through the fleece layer is relatively low and is also preferably comparatively low when urine is applied longer term or repeatedly. So as to hydrophilically modify such fleece layers, permanent conditioning agents are applied in particular in the form of emulsions to the fleece layer. In this process, cross-linking reactions with grafting of active or hydrophilic components generally take place on the surface of the fibers of the fleece. For a satisfactory application, the conditions for the cross-linking reactions, and in particular the droplet size of the emulsions, must be adjusted in a targeted manner. This procedure is very complex and expensive.

In principle, it would also be possible to apply non-permanent conditioning agents having hydrophilic components to the fibers or to the fleeces to achieve hydrophilic properties. However, such active substances are washed out of the fleece relatively quickly by aqueous media such as urine or like, and these active substances generally then work only over a disadvantageously comparatively short time period. The known measures thus have room for improvement or are in need of improvement.

In contrast, the object of the invention is to provide a use of the type mentioned above, where the above-described drawbacks can be effectively avoided. The object of the invention is in particular to provide a use in which an effective sustained-released action or storage action for active substances or active liquids, and above all also for non-permanent conditioning agents, is achieved. The object of the invention is furthermore to provide a corresponding fleece.

To attain the object, the invention initially teaches the use of a fleece composed of plastic filaments, in particular thermoplastic material, as a sustained-released system or as a storage system for at least one active substance, in particular for at least one active liquid, wherein the filaments are spun by a spinneret, wherein the plastic material of the filaments is foamed so that pores are formed at least on the surface or in the surface region of the filaments and at least some of these pores are pores that are open outward, wherein in particular at least 15%, and preferably at least 20%, of these pores are pores that are open outward, and wherein the open pores are filled at least partially with the active substance, in particular with the active liquid. The percentage information for outwardly open pores indicated here and hereafter refers in particular to the volume fraction of outwardly open pores in relation to all the pores that are formed. The volume percentage fraction of outwardly open pores is preferably determined on the basis of the absorbency of filaments having outwardly open pores for a liquid medium, as compared to the corresponding absorbency of unfoamed filaments of the same kind. The determination can take place with the aid of the oil pick up described in more detail hereafter, for example. Filaments within the scope of the invention shall be understood to mean in particular continuous filaments or continuous fibers. These continuous filaments have been applied particularly successfully within the scope of the invention, or for achieving the technical object according to the invention. Continuous filaments are known to differ from short fibers or so-called staple fibers. In principle, fleeces made of staple fibers could also be used within the scope of the use according to the invention however not preferably.

The invention is based on the discovery that the fleeces generated according to the invention are, or the pore structure of these fleeces according to the invention is, characterized by a particularly optimal storage capacity. Active substances or active liquids can be deposited in the cavities of the filaments in an effective and functionally reliable manner and also for the long term. This applies, among other things, above all to non-permanent conditioning agents having hydrophilic components. Advantageously, a longer-term sustained-released action of such active substances can be achieved.

According to particularly preferred embodiments of the use according to the invention, filaments are made from thermoplastic material, it being recommended to melt the thermoplastic material and spin the filaments in the spinneret from the molten plastic material. In principle, however, it is also within the scope of the invention that the filaments are made by wet spinning. For this purpose, it is known to dissolve the plastic material in a solvent, and the plastic material solution is then spun from the spinneret in the form of filaments.

A particularly preferred embodiment of the use according to the invention is characterized in that the active substance, or the active liquid, is at least one hydrophilizing agent or contains at least one hydrophilizing agent. The preferably employed active liquid can be a pure liquid, or a liquid solution, or a liquid mixture. It is within the scope of the invention that a non-permanent conditioning agent is applied as the hydrophilizing agent, or as an active liquid, to the filaments of the fleece or to the fleece. The hydrophilizing agent, or the non-permanent conditioning agent, is used in particular to accelerate the passage of an aqueous medium, such as the passage of urine or the like, through the fleece. In this way, the strike-through time for the passage of a liquid medium, or for the passage of a liquid aqueous medium, through the fleece can be shortened in a manner that is advantageous for many applications. This holds true in particular to applications of the fleece in a hygiene sanitary product, such as a diaper, sanitary pad or the like. In this context, the invention is based on the discovery that the pores generated according to the invention in the filaments of the fleece, and in particular the pores or open pores on the surface of the filaments, fix the active liquid, or the conditioning agent, in a functionally reliable manner so that an advantageously short strike-through time is achieved. The hydrophilizing agent, or the conditioning agent, is effectively stored in the pores of the filaments long-term.

A particularly recommended embodiment of the use according to the invention is characterized in that the active substance, or the active liquid, is at least one carboxyl compound or contains at least one organic carboxyl compound. It is recommended that the active liquid, preferably the non-permanent conditioning agent, contains at least one ester of a carboxylic acid or a fatty acid ester. Fatty acid esters have been used particularly successfully for non-permanent conditioning agents within the scope of the use according to the invention.

It is within the scope of the invention that the filaments for the fleece are made of a thermoplastic material and are spun from a spinneret, where in particular the thermoplastic material is melted and the filaments are spun from the molten plastic material by the spinneret. A particularly recommended embodiment of the use according to the invention is characterized in that the filaments, or the fleece composed of the filaments, is made by spun bonding. Here, preferably the filaments spun by the spinneret are passed through at least one quench chamber where they are subjected to a quenching medium, preferably air.

Advantageously, the filaments are subsequently fed to a stretching device. It is within the scope of the invention that the quenched and stretched filaments are deposited on a support surface, in particular on a mesh support belt or the like, to form the fleece or the spunbond fleece. Within the scope of the use according to the invention, it has proven particularly useful that the filaments are aerodynamically stretched during this spun bond process. The filaments are advantageously stretched at a stretching speed of 500 m/min to 4000 m/min. According to a particularly preferred embodiment of the invention, the spun bond process is carried out in what is known as a closed system. This means that advantageously no fluid medium is fed, or no air is fed, in the area between the quench chamber and the stretching device, or the end of the stretching device, with the exception of the quench air. It is recommended with the scope of the use according to the invention that spunbond fleece is made according to what is known as the Reicofil process, and more particularly according to the Reicofil 4 method, as the spun bond process. It is recommended that at least one diffusor is present between the stretching device and the support or the mesh support belt, the stretched or aerodynamically stretched filaments being passed through the diffusor before they are deposited on the support or on the mesh support belt. The diffusor preferably comprises at least one section diverging toward the support or the mesh support belt. In this diverging section, the side walls of the diffusor diverge toward the support or the mesh support belt. In principle, the filaments for the use according to the invention could also be made according to a melt-blown method. However, spun bonding is preferred within the scope of the use according to the invention. The filaments or fleeces made in this process are characterized by very significant advantages in terms of optimal storage capacity for the active substance, and in particular for a conditioning agent or non-permanent conditioning agent.

A particularly recommended embodiment of the use according to the invention is characterized in that the filaments for the fleece are made as multicomponent filaments, preferably from bicomponent filaments. For this purpose, the pores, or outwardly open pores, are preferably made in a component that forms the surface or the outer surface of the filaments. In this respect, the invention is based on the discovery that in this way not only an effective storage function of the fleece, but also sufficient strength or tensile strength of the filaments can be ensured. According to a particularly recommended embodiment of the use according to the invention, the multicomponent filaments or the bicomponent filaments are made in a sheath/core configuration. The pores, or outwardly open pores, are preferably formed in the sheath, or are formed solely in the sheath. In principle, it is also possible to generate the multicomponent filaments or bicomponent filaments in a side-by-side configuration within the scope of the invention, and in this case the pores, or outwardly open pores, are preferably formed only in one component on one side of the filaments.

It is within the scope of the invention that at least one foaming agent is added to the plastic material for the filaments, in particular to the plastic material melt for the filaments, and more particularly is added such that pores are formed at least on the surface of the filaments, of which it is recommended that at least 15% and preferably at least 20%, are pores that are open outward. The thermoplastic material for the filaments is advantageously melted in at least one extruder. It is within the scope of the invention that the at least one foaming agent is added in the extruder, or is added to the melt of the thermoplastic material in the extruder. If, according to a preferred embodiment within the scope of the use according to the invention, multicomponent filaments and especially bicomponent filaments are made, the foaming agent is advantageously added only to one component, or is added only to one component in the associated extruder.

According to one embodiment of the use according to the invention, a fluid, in particular a compressed gas or a compressed inert gas, is added as the foaming agent. This fluid is preferably compressed carbon dioxide or compressed nitrogen. It is within the scope of the invention that the compressed fluid is added in the extruder, or is added to the melt of the thermoplastic material in the extruder. It is further within the scope of the invention that the compressed fluid dissolves in the plastic material melt at the pressure that is present in the extruder. For example, 0.03 to 0.20 g carbon dioxide per gram of polypropylene is dissolved under extrusion conditions in the extruder of 180° C. to 300° C. and at a pressure of 30 to 200 bar. When the plastic material melt exits the spinneret, the pressure drops so that the foaming agent or the physical foaming agent can no longer remain in solution and becomes gaseous. This results in the formation of bubbles that migrate in particular to the filament surface. As the melt cools, the bubbles are essentially frozen in place and remain in the filaments as pores or as a pore structure. Depending on the extrusion conditions, in particular depending on the pressure and/or temperature and/or rate at which the pressure drops and/or the amount and/or type of compressed fluid that is added, the pore size and pore count, and in particular the number of pores that are open outward as well as the specific surface area of the filaments, and thus the storage capacity of the filaments, can be adjusted in a targeted manner.

According to another preferred embodiment of the use according to the invention, a decomposable chemical foaming agent is added, or is added to the melt of the thermoplastic material in an extruder. If, according to a particularly recommended embodiment of the invention, multicomponent filaments or in particular bicomponent filaments are made, the decomposable chemical foaming agent is advantageously added only to the component, or only in the extruder associated with the component, in which the pores are to be made by foaming. The decomposable chemical foaming agent is in particular at least one substance from the group "decarboxylation substance, Azo compound, and hydrazine compound." It is within the scope of the invention that a gas, in particular carbon dioxide or nitrogen, is created in the melt or in the plastic material melt during decomposition of the chemical foaming agent, and thus bubbles are formed in the melt, so that pores are obtained, or a pore structure is obtained, when the plastic material cools or the filaments cool. Decarboxylation substance within the scope of the invention shall be understood to mean a decomposable chemical foaming agent whose chemical decomposition generates carbon dioxide. According to a particularly preferred embodiment of the use according to the invention, but without limiting same, a citric acid derivative is used as the decomposable chemical foaming agent, or as the decarboxylation substance. Advantageously, 0.1% by weight to 10% by weight, preferably 1% by weight to 10% by weight, of a master batch having the decomposable chemical foaming agent is added to the melt or to the plastic material melt. Master batch here shall be understood to mean in particular that the decomposable chemical foaming agent is dissolved in at least one plastic material, or is mixed with at least one plastic material. It is recommended that the plastic material contains 15% by weight to 50% by weight, and preferably 15% by weight to 45% by weight, of the decomposable chemical foaming agent. According to a recommended embodiment, the plastic material is a polyolefin, in particular a polyethylene or a polypropylene.

It is within the scope of the invention that the active substance or the active liquid is applied to the fleece after the filaments have been deposited on a support, in particular on a mesh support belt. It is recommended that the application is carried out after the fleece has been calendered, or after the fleece has passed through at least one calendering device. According to a highly recommended embodiment of the invention, at least one non-permanent conditioning agent is applied to the fleece, or to the calendered fleece, and preferably a non-permanent conditioning agent is applied as the hydrophilizing agent to the fleece. The active substance or the active liquid can be applied in line to the fleece on the support surface, or it can be applied offline at a later time. According to one embodiment variant, an active liquid, or a liquid conditioning agent, or a non-permanent conditioning agent, can be applied to the fleece with the aid of spray nozzles, or also by a kiss-roll application process, or within the scope of a foam application. It is within the scope of the invention that the fleece, together with the active liquid applied thereto, is subsequently dried.

According to a highly recommended embodiment of the use according to the invention, foaming takes place only on the surface of the filaments, so that pores are present, or a pore structure is present, only on the surface or in surface regions of the filaments. The preferred embodiment described above has been tried and tested for this purpose, according to which the multicomponent filaments, and in particular bicomponent filaments are made, in which the foaming takes place, or the pores are present, only in an outer component or in the sheath. The thickness of the foamed surface layer, or of the pore-containing surface layer, of the filaments is advantageously 5% to 50%, preferably 15% to 40%, and particularly preferably 25% to 35% of the filament diameter. It is within the scope of the invention that the inner region of the filaments located beneath the pore-containing surface layer is not foamed, and that this inner region has no or almost no pores.

The subject matter of the invention further relates to a fleece, or to a spunbond fleece, composed of filaments, made in particular of plastic material, and foamed regions having pores are present at least on the surface, or the outer surface, of the filaments, of which at least some are pores that are open outward, where preferably at least 15%, preferably at least 20%, and particularly preferably at least 30% are pores that are open outward, and the fineness of the filaments is 0.25 den to 15 den, in particular 0.25 den to 5 den, and the specific surface area of the filaments is 20 $mm^2/m$ to 400 $mm^2/m$. It is within the scope of the invention that the fleece is, or the filaments are, made such that the at least one foaming agent is added such that the above-described number of pores, or of pores that are open outward, is formed at least on the surface or on the outer surface of the filaments so that the specific surface area of the filaments is 20 $mm^2/m$ to 400 $mm^2/m$ at a filament fineness of 0.25 den to 15 den, in particular at a filament fineness of 0.25 den to 5 den. The volume, or the total volume, of the pores in the foamed regions of the filaments is preferably 0.5% to 60%, in particular 40% to 60%. The diameter of the pores is advantageously smaller than or equal to 15% of the filament diameter. It is recommended that the diameter of the pores is 1% to 12% of the filament diameter. It is within the scope of the invention that the filaments of the fleece are made from at least one plastic material from the group "polyethylene, polypropylene, and polyester." The polyester used is preferably polyethylene terephthalate (PET). In principle, however, it is also possible to use other thermoplastic materials, or mixtures of thermoplastic materials, within the scope of the invention. Advantageously the filaments made of at least one plastic material from the group "polypropylene (PP), polyethylene (HDPE, LDPE, LLDPE), polystyrene (PS), acrylonitrile butadiene styrene (ABS), polyethylene terephthalate (PET), polyethylene terephthalate glycol-modified (PETG), polycarbonate (PC), thermoplastic elastomer (TPE), thermoplastic polyurethane (TPU), a mixture of rubber and thermoplastic materials (TPR), polyamide (PA), and polyvinyl chloride (PVC)" are used.

The invention is based on the discovery that the use according to the invention, or the fleece made according to the invention, and the pore structure present in particular on the surface/outer surface of the filaments allow particularly advantageous effects to be achieved. The filaments or the fleeces can be used excellently as a sustained-released system or storage system for active substances, and in particular for active liquids. The storage capacity is surprisingly high. The active substances, or the active liquids, can advantageously be fixed long-term in the filaments or fleeces, and thus ensure the desired properties of the filaments/fleeces in the long term. The fleeces made according to the invention have been tried and tested in particular in connection with the application of non-permanent conditioning agents. The conditioning agent constituents are retained in the pore structure of the fleeces or filaments in a functionally reliable manner, so that they are also resistant to washout, discharge or the like in the long run. It is assumed that, while the conditioning agent constituents can be washed off or washed out of the surface of the filaments at least partially, conditioning agent is basically resupplied from the pores or migrates from the pores to the surface of the filament. In this respect, the implementation of the measures according to the invention basically turns a non-permanent conditioning agent into a permanent conditioning agent. This is particularly advantageously above all when using hydrophilically modified fleece layers. The fleece layers that are hydrophilically modified in particular with the aid of conditioning agents that are not permanent per se are characterized by a short or marginal strike-through time, in particular with respect to aqueous media such as urine or the like. This advantageous property is also preserved longer term, and when the aqueous medium is repeatedly applied, when the measures according to the invention are implemented. These hydrophilically modified fleece layers are therefore suitable in particular for use in diapers, sanitary pads or similar hygiene products. According to the invention, an advantageously short strike-through time is achieved in such modified fleece layers, or hydrophilically modified fleece layers.

The filaments according to the invention, or the fleeces according to the invention, can also very advantageously be used for a slow, basically controlled released of the active substance. In this connection it should be pointed out that the filaments or fleeces made according to the invention can also be used as effective storage systems for other active substances, for example for medically or pharmaceutically active substances or for skin care products, detergents or the like. The properties of the fleeces made according to the invention can easily be adapted using appropriate active substances and can be formulated to be hydrophilic or also hydrophobic in a functionally reliable manner. When such fleeces are used as filter media, the filtration performance can surprisingly be drastically increased as a result of the pores in the filaments. Given the relatively high specific surface area of the fleeces made according to the invention, it is also possible to modify fleece properties such as hand or roughness or the like in a targeted manner. In spunbond nonwoven fabrics, the higher specific surface area also results in a better bonding ability when bonding the filaments. Very good adhesion between the filaments can also be achieved when compacting the fleeces by needling, in particular by hydro-needling. Moreover, the fleeces made according to the invention are easily imprintable due to the high surface area. Fleeces made by the method according to the invention can also be used as scouring cloths and the like. It should also be emphasized that the fleeces can be made easily and cost-effectively by the method according to the invention.

The invention will be described in more detail below with reference to drawings showing only one embodiment. Shown are the following, in schematic illustrations:

FIG. 2 is a perspective view of a filament according to the invention;

FIG. 3 is a section through the filament of FIG. 2;

Figure 1:
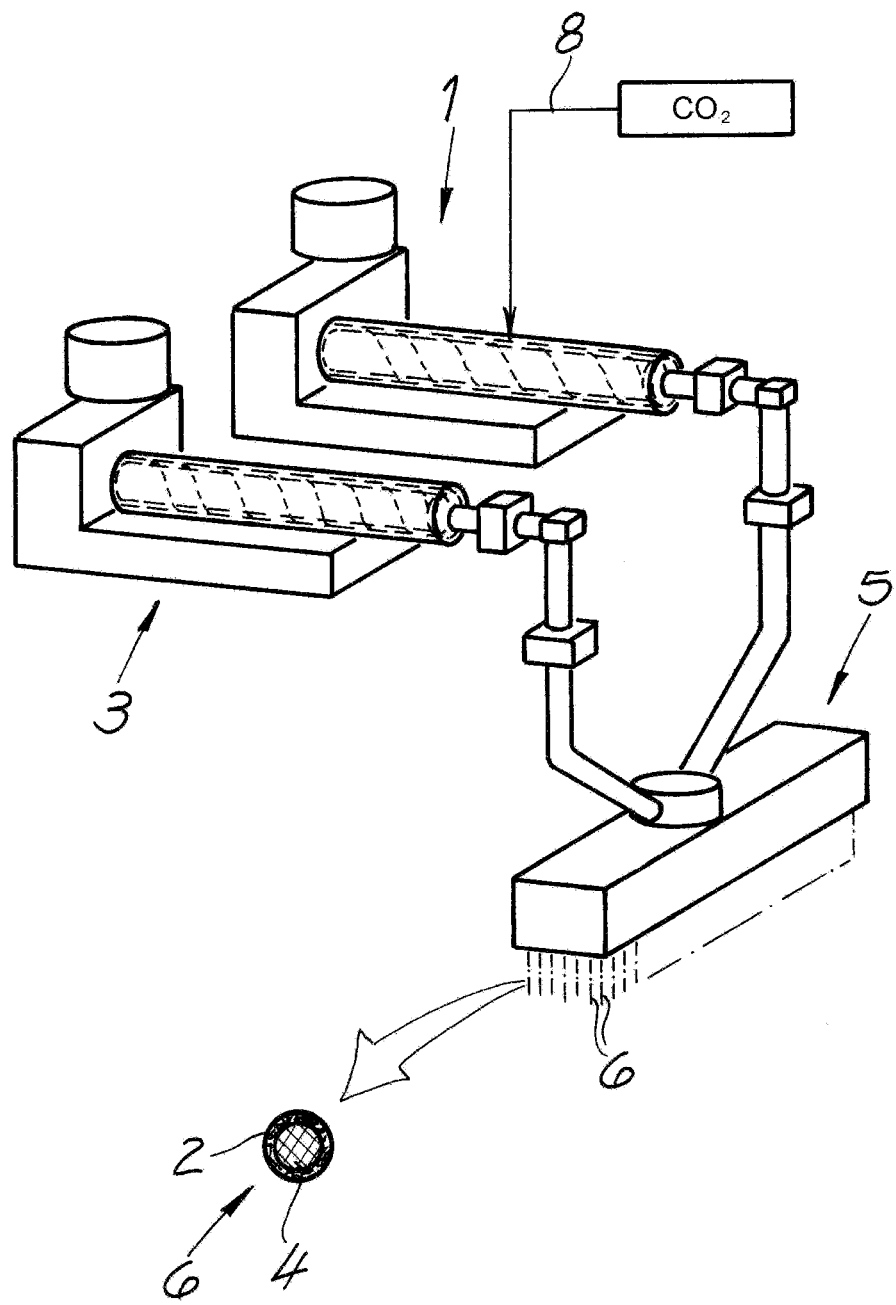
FIG. 1 is a perspective view of an apparatus for making a fleece according to the invention.

FIG. 1 shows an apparatus for making a spunbond fleece composed of thermoplastic filaments by spun bonding. The filaments are bicomponent filaments 6 having a sheath/core configuration. The apparatus comprises a first extruder 1 for melting the thermoplastic material for the sheath 2, and a second extruder 3 for melting the thermoplastic material of the core 4. The two plastic material melts are conducted out of the extruders 1 and 3 and fed to a spinneret 5 whence the bicomponent filaments 6 are spun in the sheath/core configuration.

Preferably and in the illustrated embodiment, the sheath 2 is foamed so that pores 7, in particular pores 7a that are open outward, are formed in the sheath 2 and on the surface of the bicomponent filaments 6. Advantageously and in the illustrated embodiment, compressed liquid carbon dioxide is fed for this purpose to the plastic material melt for the sheath 2 in the first extruder 1, more particularly via a feed line 8. The compressed fluid dissolves in the plastic material melt at the pressure present in the extruder 1. The pressure drops when the plastic material melt exits the spinneret 5, and the compressed carbon dioxide cannot remain in solution and becomes gaseous. This creates bubbles that migrate to the surface of the bicomponent filaments 6, among other things. When the plastic material melt cools, the bubbles are frozen in place and are preserved in the filaments in the form of pores 7, 7a.

FIGS. 2 and 3 show a bicomponent filament 6 made according to the invention, having pores 7 or open pores 7a in the sheath 2. It is discernible that a plurality of pores 7a that are open outward are disposed on the outer surface of the sheath 2. In this way, an advantageously high specific surface area of the bicomponent filaments 6 is achieved. At least 20%, preferably at least 30%, of the pores 7 that are formed on the surface or on the outer surface of the bicomponent filaments 6 are preferably pores 7a that are open outward. It is recommended that the pore diameter d be 1% to 12% of the diameter D of the bicomponent filaments 6. In the illustrated embodiment, the pore diameter d may range between 2.2 and 4 µm. FIG. 3 incidentally shows separate or mutually separated pores 7. In principle, at least some of the pores 7, 7a can also be connected among each other.

Within the scope of the invention, the pores 7a that are open outward and present on the filament surface are of particular significance. An active substance, or an active fluid, can be accommodated and fixed in a functionally reliable manner in particular in outwardly open pores. In the illustrated embodiment (FIG. 3), a non-permanent conditioning agent 9 is accommodated in these pores 7a of the bicomponent filaments 6 that are open outward as the hydrophilizing agent. In this way, filaments or fleeces that are hydrophobic per se are hydrophilically modified. The non-permanent conditioning agent 9 is fixed in a functionally reliable manner in particular in the pores 7a of the fleece that are open outward, so that they are essentially resistant to washout, discharge and the like also in the long term. It is assumed that, while the conditioning agent can be washed off or washed out of the pore-free filament surface at least partially, conditioning agent is resupplied from the open pores 7a or basically migrates to the filament surface. This results in an advantageously low strike-through time for a fleece layer that is provided with the non-permanent conditioning agent 9, in particular for aqueous media such as urine or the like. Such a hydrophilically modified fleece layer according to the invention is therefore suitable primarily for use in diapers and similar hygiene products.

EXAMPLE

A reference fleece (1075) comprising unfoamed filaments and two spunbond fleeces according to the invention (1090 and 1089) comprising foamed filaments were made by a spun bond process, namely the Reicofil 4 method. The filaments were made from polypropylene, and more particularly from the commercially available polypropylene raw material 561 R. Table 1 below indicates the settings for the spun bond process as well as the measurement results for the three spunbond fleeces.

The filaments for the spunbond fleeces according to the invention were made by an apparatus according to FIG. 1, using the two extruders 1 and 3 to make bicomponent filaments 6 having a sheath/core configuration. Both components were made of the above-described polypropylene. A decomposable chemical foaming agent, namely Hydrocerol 40, was added in the first extruder 1 only to the plastic material or the plastic material melt for the sheath 2. This is a master batch comprising a decomposable chemical foaming agent. In this master batch, 40% by weight of a citric acid derivative is dissolved as the decomposable chemical foaming agent in polyethylene (LDPE). Column 2 of Table 1 indicates the concentration of Hydrocerol 40 in the sheath 2 in % by weight. The foaming of the sheath 2 took place immediately upon exiting of the filaments from the spinneret 5. The core/sheath weight ratio of the foamed filaments was 70/30. The reference spunbond fleece was also made by an apparatus according to FIG. 1. The two extruders 1 3 were also employed for this purpose. However, no foaming agent was added here.

Column 3 shows the extrusion temperature for the filaments of all spunbond fleeces. The filaments were extruded from a spinneret and subsequently conducted through a quench chamber for quenching the filaments. Column 4 shows the respective blowing temperature for the quench chamber. Column 5 indicates the adjusted thread speed or filament speed in m/min.

The total surface area (Column 6) was determined in m$^2$/g by measuring the average (n=10) diameter (Columns 8 and 9) of the filaments deposited on the mesh belt based on the cross-section. On the basis of the known throughput and the known filament count, the filament length is obtained via the optically determined titer in [den] (titer in [den] corresponds to [g/9000 m] (T[den]=0.9 d[μm]$^2$ r[g/cm$^2$]p 1/400). The total surface area of the unfoamed filaments results from the circumference and the cylinder length. For a foamed filament, the average (n=10) number of pores in the cross-section was counted and the average (n=10) diameter thereof was measured. Cylindrical pores were assumed for the porosity. The measuring method only allows pores to be determined in the cross-section of the filaments, and the pores thus appear as circular voids. Because the filaments are subjected to this, it is to be assumed that the spherical pore at the spinneret exit turns into a cylindrical pore, which has the maximal length of the pore diameter×warpage.

The porosity (Columns 10 and 11) was calculated by relating the sum of the cross-sectional surface of all pores of a cutting plane to the cross-sectional surface of the total filament, or only the sheath surface.

The pick-up behavior was determined on the basis of oil pick up (OPU) using Silastol 163 in an aqueous emulsion. This is a non-permanent conditioning agent composed of hydrophilic components and wetting agents. The gravimetrically determined OPU was calculated from the ratio between the mass of the spunbond fleeces without conditioning agent and the mass of the dried spunbond fleeces with conditioning agent.

Figure 4:
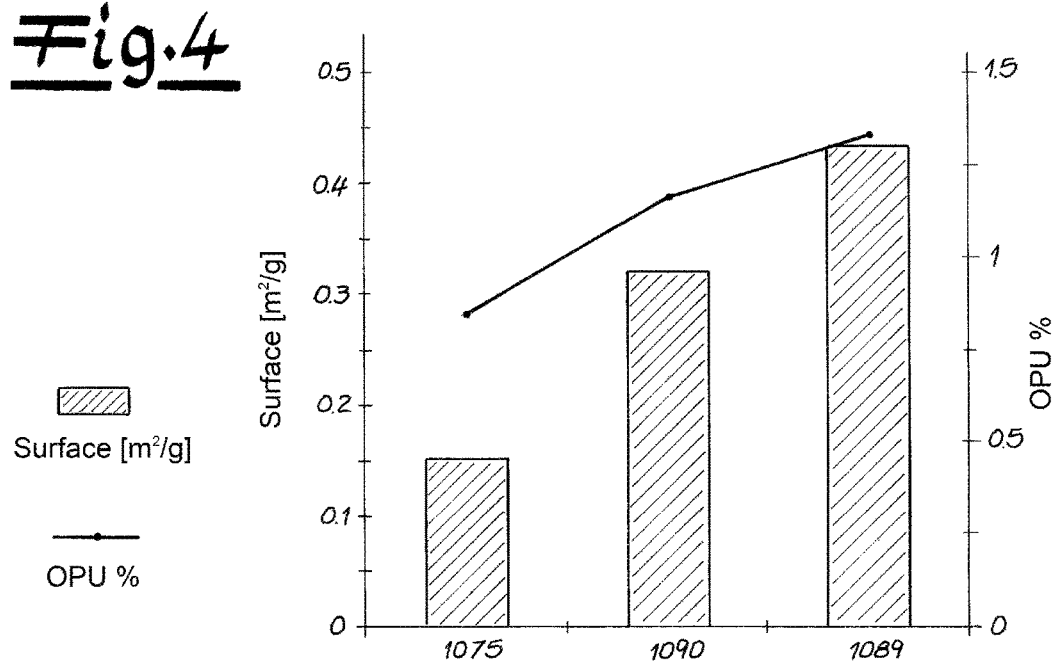
FIG. 4 is a first diagram of the illustrated embodiment.

FIG. 4 shows the total surface area in m$^2$/g and the OPU in percent for the three spunbond fleeces (1075, 1090 and 1089). It is apparent from FIG. 4 and Table 1 that the total surface area of the first spunbond fleece (1090) comprising foamed filaments is enlarged by more than 100% compared to the spunbond fleece comprising unfoamed filaments (1075). In the second spunbond fleece (1080) comprising foamed filaments, the total surface area is almost triple that of the spunbond fleece (1075) comprising unfoamed filaments. The increase in the total surface areas correlates with the increase in the absorbency for the conditioning agent. The OPU is increased from 0.84% in the spunbond fleece (1075) comprising unfoamed filaments to 1.17% and 1.33% in the spunbond fleeces (1089 and 1090) comprising foamed filaments.

Figure 5:
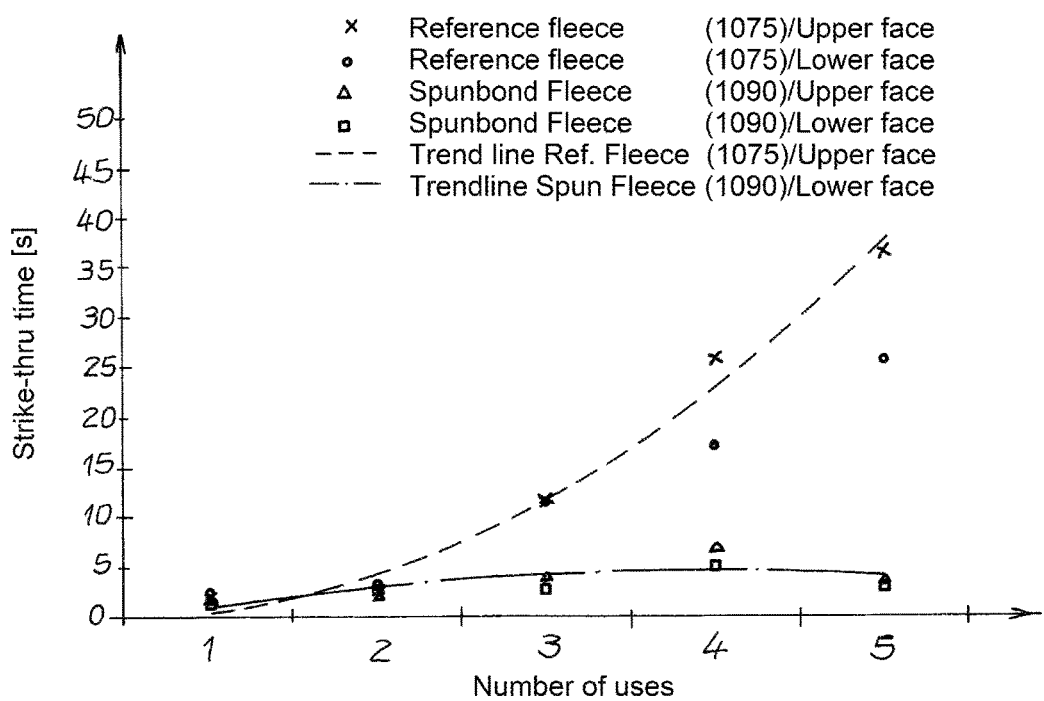
FIG. 5 is a second diagram of the illustrated embodiment.

FIG. 5 shows the measurement results for a multiple strike-through test for a reference fleece (1075) and for a spunbond fleece made according to the invention (1090). This test is specified in more detail in ISO 9073-8 (1995). In this test, the strike-through time through the spunbond fleece (here: 1075 and 1090) to be tested is measured. A defined volume of a liquid (simulated urine: here 0.9% by weight aqueous salt solution) is applied to the surface of fleece. Beneath the spunbond fleece, in contact with the spunbond fleece, is a standardized absorbent cellulose cushion that absorbs the liquid passing through the spunbond fleece. A 5 ml portion of the aqueous solution was applied in each case five times to a spunbond fleece, and more particularly both from the upper face of the spunbond fleece and from the lower face of the spunbond fleece. The diagram according to FIG. 5 shows the strike-through time as a function of the number of times the liquid is applied to the spunbond fleece. The dotted curve represents the reference fleece (1075) comprising unfoamed filaments. Here, the hydrophilizing agent, or the non-permanent conditioning agent, is consumed quickly with multiple applications of the liquid to the spunbond fleece, such that the strike-through time through the spunbond fleece increases significantly. In contrast, the dot-dash curve represents a fleece (1090) according to the invention comprising foamed filaments. It is discernible that a low strike-through time is ensured even with multiple applications of the liquid. Here, the hydrophilizing agent, or the non-permanent conditioning agent, is stored effectively in the pores of the filaments, and thus the hydrophilic properties of the spunbond fleece can be ensured in a lengthy or long term. As was already shown above, such a fleece layer modified according to the invention is in particular advantageous for diapers or the like. A hydrophilically modified fleece layer according to the invention allows the urine in diapers to basically be removed quickly, and in particular to be fed to an absorbent core made of cellulose or the like.

TABLE 1

Process settings and results for a reference spunbond fleece and for two spunbond fleeces according to the invention:

| | | Process | | | | Results | | | | | | |
| --- | --- | --- | --- | --- | --- | --- | --- | --- | --- | --- | --- | --- |
| | | | | | | Column | | | | | | |
| | | | | | | | | | | 10 Pore surface/ total cross-section [%] | 11 Pore surface/ sheath cross-section [%] | |
| Explanation | 1 Sample no. | 2 Conc. Hydrocerol 40 wt. % | 3 Extrus. Temp. ° C. | 4 Blowing Temp. ° C. | 5 Set filament speed m/min | 6 Total surface area [m$^2$/g] | 7 Total surface area [mm$^2$/m] | 8 Filament diameter [μm] | 9 Filament diameter [den] | | | 12 Gravimetric OPU [%] |
| Unfoamed filaments | 1075 | 0 | 220 | 20 | 2550 | 0.15 | 97.39 | 31 | 6.2 | 0.00 | 0.00 | 0.84 |

TABLE 1-continued

Process settings and results for a reference spunbond fleece and for two spunbond fleeces according to the invention:

| | | Process | | | | | | Results | | | | |
|---|---|---|---|---|---|---|---|---|---|---|---|---|
| | | | | | | | | Column | | | | |
| Explanation | 1 Sample no. | 2 Conc. Hydrocerol 40 wt. % | 3 Extrus. Temp. ° C. | 4 Blowing Temp. ° C. | 5 Set filament speed m/min | 6 Total surface area [m²/g] | 7 Total surface area [mm²/m] | 8 Filament diameter [μm] | 9 Filament diameter [den] | 10 Pore surface/ total cross-section [%] | 11 Pore surface/ sheath cross-section [%] | 12 Gravimetric OPU [%] |
| Foamed filaments | 1090 | 4.5 | 220 | 20 | 2550 | 0.32 | 203.87 | 31 | 6.2 | 13.97 | 46.56 | 1.17 |
| Foamed filaments | 1089 | 4.5 | 220 | 20 | 2300 | 0.43 | 276.41 | 32 | 6.6 | 21.74 | 72.46 | 1.33 |

The invention claimed is:

1. A method of making a fleece for sustained-released system or storage of an active liquid, the method comprising the steps of:
   spinning from a plastic material continuous bicomponent core/sheath filaments by a spinneret;
   foaming the plastic material only of the sheaths of the continuous filaments so that pores are formed in the sheaths at least on a surface of the continuous filaments and at least 15% of the pores open outward;
   using a nonpermanent conditioning agent as the active liquid;
   filling the open pores at least partially with the active liquid; and
   forming the continuous filaments into the fleece.

2. The method defined in claim 1, wherein the active liquid is at least one hydrophilizing agent or contains at least one hydrophilizing agent.

3. The method defined in claim 1, wherein the active liquid contains at least one carboxyl compound.

4. The method defined in claim 1, wherein the fleece composed of the continuous filaments is formed by spun bonding by passing the continuous filaments spun by the spinneret through at least one quench chamber where they are subjected to quench air, and subsequently stretching the continuous filaments in a stretching device.

5. The method defined in claim 4, wherein the continuous filaments are stretched at a stretching speed of 500 m/min to 4000 m/min.

6. The method defined in claim 1, wherein the plastic material is foamed by adding at least one foaming agent to the plastic material from which the sheaths of the continuous filaments are spun such that the pores that open outward are formed at least on an outer surface of the sheaths of the continuous filaments.

7. The method defined in claim 6, the plastic material is foamed by adding a foaming agent to an extruder connected to the spinneret.

8. The method defined in claim 1, further comprising the steps of:
   depositing the continuous filaments on a support before filling the open pores with the active liquid and after calendering of the fleece.

9. The method defined in claim 1, wherein:
   a fineness of the continuous filaments is 0.25 den to 15 den, and
   a specific surface area of the continuous filaments is 20 mm²/m to 400 mm²/m.

10. The method defined in claim 1, wherein a volume of the pores in the sheaths is 0.5% to 60%.

11. The method defined in claim 1, wherein a diameter of each of the pores is smaller than or equal to 15% of a diameter of the filament.

12. The method defined in claim 11, wherein the diameter of each of the pores is 1% to 12% of the filament diameter.

13. A method of making a fleece comprising the steps of:
   providing two supplies of a spinnable plastic material;
   adding a foaming agent to the material of only one of the two supplies;
   spinning the materials of both supplies together from a spinneret to form sheath/core bicomponent continuous filaments whose sheaths are formed by the material containing the foaming agent such that as the materials exit the spinneret the foaming agent expands and forms only in the sheath pores of which at least 15% are outwardly open;
   forming the spun continuous filaments into a fleece; and
   at least partially filling the open pores with an active liquid consisting of a nonpermanent conditioning agent.

14. The method defined in claim 13, wherein at least 25% of the pores are outwardly open.

15. The method defined in claim 13, wherein the active liquid is or contains a hydrophilizing agent.

16. The method defined in claim 13, wherein the materials are selected such that the cores of the bicomponent filament are of greater tensile strength than the sheaths.

17. The method defined in claim 13, further comprising after spinning the continuous filaments the substeps of:
   quenching the continuous filaments; and
   stretching the continuous filaments,
the fleece being formed by the substeps of:
   depositing the stretched bicomponent continuous filaments on a support; and
   calendering together the bicomponent continuous filaments on the support, the open pores being filled after calendering.

* * * * *